(12) United States Patent
Rooney et al.

(10) Patent No.: US 7,198,703 B2
(45) Date of Patent: Apr. 3, 2007

(54) CHAMBER-FORMING ELECTROPHORESIS CASSETTE COVER

(75) Inventors: Regina D. Rooney, La Jolla, CA (US); Bradley S. Scott, San Diego, CA (US); Thomas R. Jackson, La Jolla, CA (US); Joseph W. Amshey, Encinitas, CA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 10/870,131

(22) Filed: Jun. 16, 2004

(65) Prior Publication Data

US 2005/0023139 A1    Feb. 3, 2005

Related U.S. Application Data

(60) Provisional application No. 60/504,389, filed on Sep. 19, 2003, provisional application No. 60/479,345, filed on Jun. 17, 2003.

(51) Int. Cl.
*G01N 27/447* (2006.01)

(52) U.S. Cl. ............... 204/606; 204/456; 204/610; 204/459

(58) Field of Classification Search ........ 204/456–470, 204/606–621; 435/305.1–305.4; 422/58, 422/68.1, 100; 73/431
See application file for complete search history.

(56) References Cited

U.S. PATENT DOCUMENTS 3,766,047 A * 10/1973 Elevitch ............... 204/469

| | | | | |
|---|---|---|---|---|
| 4,849,078 A | * | 7/1989 | Love et al. ............ | 204/464 |
| 4,944,483 A | * | 7/1990 | Nishizawa ............ | 249/83 |
| 5,543,023 A | * | 8/1996 | Lugojan ............... | 204/618 |
| 6,113,766 A | | 9/2000 | Steiner et al. | |
| 6,156,182 A | * | 12/2000 | Olech et al. ......... | 204/610 |
| 6,599,410 B1 | | 7/2003 | Steiner et al. | |
| 6,696,021 B1 | * | 2/2004 | Bertling ............... | 422/68.1 |
| 2003/0015426 A1 | | 1/2003 | Rooney et al. | |

FOREIGN PATENT DOCUMENTS

| | | | | |
|---|---|---|---|---|
| WO | WO 98/57162 | 12/1998 | | |
| WO | WO 01/20315 A1 | * | 3/2001 | ......... 204/456 |
| WO | WO 02/092200 | 11/2002 | | |
| WO | WO 03/029523 A1 | * | 4/2003 | ......... 204/606 |

OTHER PUBLICATIONS

3M Corporation, "Pressure Sensitive Adhesive Bonding Solutions" product brochure, 2000.*
Rabilloud et al., "Sample Application by In-gel Rehydration Improves the Resolution of Two-dimensional Eletrophoresis with Immobilized pH Gradient in the First Dimension," Electrophoresis, 15(12):1552-8 (1994).

* cited by examiner

*Primary Examiner*—Nam Nguyen
*Assistant Examiner*—Jeffrey Barton

(57) ABSTRACT

A multielevational cover for assembling a fluid retaining chamber on a face of an electrophoresis cassette is presented. The cover comprises a cassette-containing member, at least one chamber-defining member, and sealing means, typically sealing means that are capable of reversible attachment. Also presented are methods for contacting cassette-immobilized gels to desired fluids by assembling a fluid retaining chamber upon the cassette using the covers of the present invention.

31 Claims, 17 Drawing Sheets

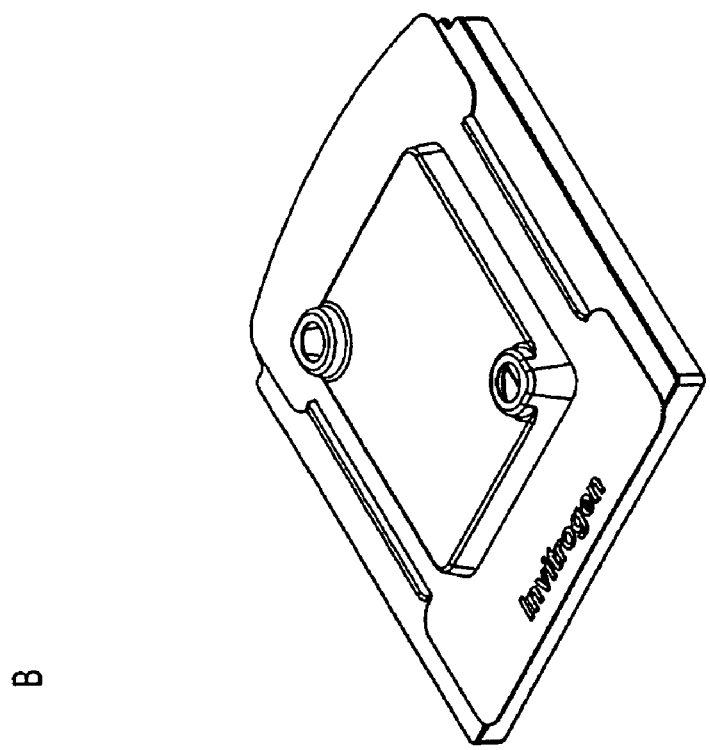
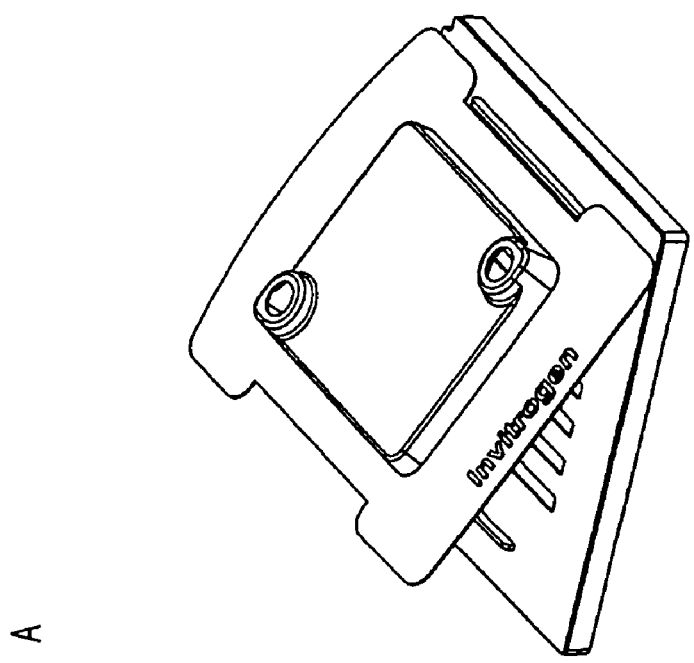
FIG. 17

CHAMBER-FORMING ELECTROPHORESIS CASSETTE COVER

FIELD OF THE INVENTION

The present invention is in the field of devices, components, and methods for electrophoresis, particularly two dimensional polyacrylamide gel electrophoresis (2D-PAGE).

BACKGROUND OF THE INVENTION

Two dimensional gel electrophoresis (2D-PAGE) is currently a method of choice for analysis of complex proteomes, permitting the separation, identification, and analysis of large numbers of proteins in a single multiplexed analysis.

Typically, first dimension separation is performed by isoelectric focusing within the gel of an immobilized pH gradient (IPG) strip. Subsequent equilibration, typically by contacting the IPG strip with fluid buffers variously containing reducing and alkylating agents, prepares the focused proteins for second dimension size separation on a polyacrylamide gel.

The recent development of cassettes within which IPG strips can be hydratingly lodged during focusing—as described for example in U.S. patent application publication No. 2003/0015426 and international patent publication no. WO 02/092200, and available commercially from Invitrogen Corp. as the ZOOM® IPGRunner™ system—has significantly simplified first dimension separation.

Notwithstanding these improvements during first dimension separation, however, the subsequent step of equilibration requires that IPG strips be individually removed from the cassette and placed in separate tubes, within which they can be equilibrated in preparation for second dimension separation. The tubes add cost, and handling the strips increases the chance of damage to the strips and the gels thereon, with consequent loss of analytical resolution.

There thus exists a need in the art for apparatus and methods that permit the contact of cassette-immobilized gels to fluids, such as equilibration fluids, without requiring their removal from the cassettes within which or upon which they are immobilized.

SUMMARY OF THE INVENTION

The present invention solves these and other needs in the art by providing, in a first aspect, a cover—synonymously, a "tray"—for assembling at least one fluid retaining chamber on a face of an electrophoresis cassette.

The cover comprises a cassette-contacting member, at least one chamber-defining member, and sealing means. A first face of the cassette-contacting member is in surface continuity with a first face of each chamber-defining member, the continuous surface defining a first face of the cover. A second face of the cassette-contacting member is in surface continuity with a second face of each chamber-defining member, the continuous surface defining a second face of the cover. The cassette-contacting member is disposed circumferentially around each chamber-defining member at a first elevation of the cover and the sealing means is disposed circumferentially around each chamber-defining member on the cassette-contacting member first face.

Each chamber-defining member elevates the cover first face in the direction of the cover second face to at least a second cover elevation.

In one series of embodiments, the cover has a single chamber-defining member. In other embodiments, the cover has a plurality of chamber-defining members, such as six chamber-defining members.

In some embodiments, each chamber-defining member has at least one fluid port, the fluid port boring through both the first and second cover faces. In some embodiments, each chamber-defining member has a single fluid port; in certain embodiments, the fluid port can occupy a substantial portion of the chamber defining member. In other embodiments, each chamber-defining member has a plurality of fluid ports, such as two fluid ports, the additional fluid ports usefully acting as vents.

The cover can be of integral manufacture, in which the cassette-contacting member is integral to each chamber-defining member. In such embodiments, the cover usefully can be molded from a single part.

For example, the cover can be molded in a single piece from a plastic, such as a thermoformable plastic selected from the group consisting of polypropylene, polyethylene, and polyvinylchlorides. In other embodiments, the cover can be injection molded from an injection moldable plastic, such as a plastic selected from the group consisting of polycarbonate, polystyrene, acrylic, ABS, polyvinylchloride, polypropylene, polyethylene and plasticized alloys of each.

Molded pieces can additionally be milled or further worked after molding.

In typical embodiments, the sealing means includes at least one adhesive layer, such as a layer having an acrylic adhesive or a rubber adhesive. In one series of embodiments, the sealing means includes an acrylic adhesive disposed on both sides of a polyethylene or polyvinylchloride tape.

In another aspect, the invention provides a method of contacting a gel that is immobilized within or upon a cassette to a fluid volume.

The method comprises assembling at least one fluid retaining chamber on a first face of an electrophoresis cassette, the first cassette face being in fluid communication with said gel; and then introducing a fluid into the chamber. The cover can usefully be any of the cover embodiments presented herein.

In some embodiments, the method further comprises the antecedent step of bringing the gel into fluid communication with a first face of the cassette. In embodiments of the method in which the gel is part of an immobilized pH gradient (IPG) strip, the cassette can usefully be an IPGRunner™ cassette (Invitrogen Corp., Carlsbad, Calif., USA). In such embodiments, the gel is brought into fluid communication with a first face of the cassette by exposing the entire longitudinal length of the channels within the cassette, and thus the entire longitudinal length of the strips resident therein, by removing well forming members after rehydration of the strips and prior to focusing, and then removing the laminar film cover after focusing.

In another aspect, the invention provides a kit comprising one or more covers (synonymously, "trays") for assembling a fluid retaining chamber on a face of an electrophoresis cassette.

In some embodiments, the kit comprises at least one cover and at least one electrophoresis cassette, the cover typically being adapted to contact the cassettes packaged therewith. In some embodiments, the cassette has means for hydratingly lodging a prior-cast electrophoretic separation medium within an assembled enclosing member; and means for spaced electrical communication with the enclosed medium, the spaced electrical communication means useful to establish a voltage gradient in the enclosed separation medium sufficient to effect electrophoretic separation of analytes therein; in some of these embodiments, the cassette is an IPGRunner cassette from Invitrogen Corp. (Carlsbad, Calif., USA).

The kits can comprise one or more fluid solutions, such as solutions useful for denaturing, reducing, and/or alkylating protein analytes, or a solution containing one or more enzyme substrates for detection, visualization, and/or quantification of one or more enzymes present within the separation medium.

In various embodiments, the kits comprise separation media, such as IPG strips, either separately packaged or contained within or disposed upon one or more cassettes.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIGS. 17A and 17B illustrate a process for aligning and applying a cover of the present invention to an electrophoresis cassette.

DETAILED DESCRIPTION OF THE INVENTION

In a first aspect, the invention provides a cover for assembling at least one fluid retaining chamber on a face of an electrophoresis cassette.

Figure 4:
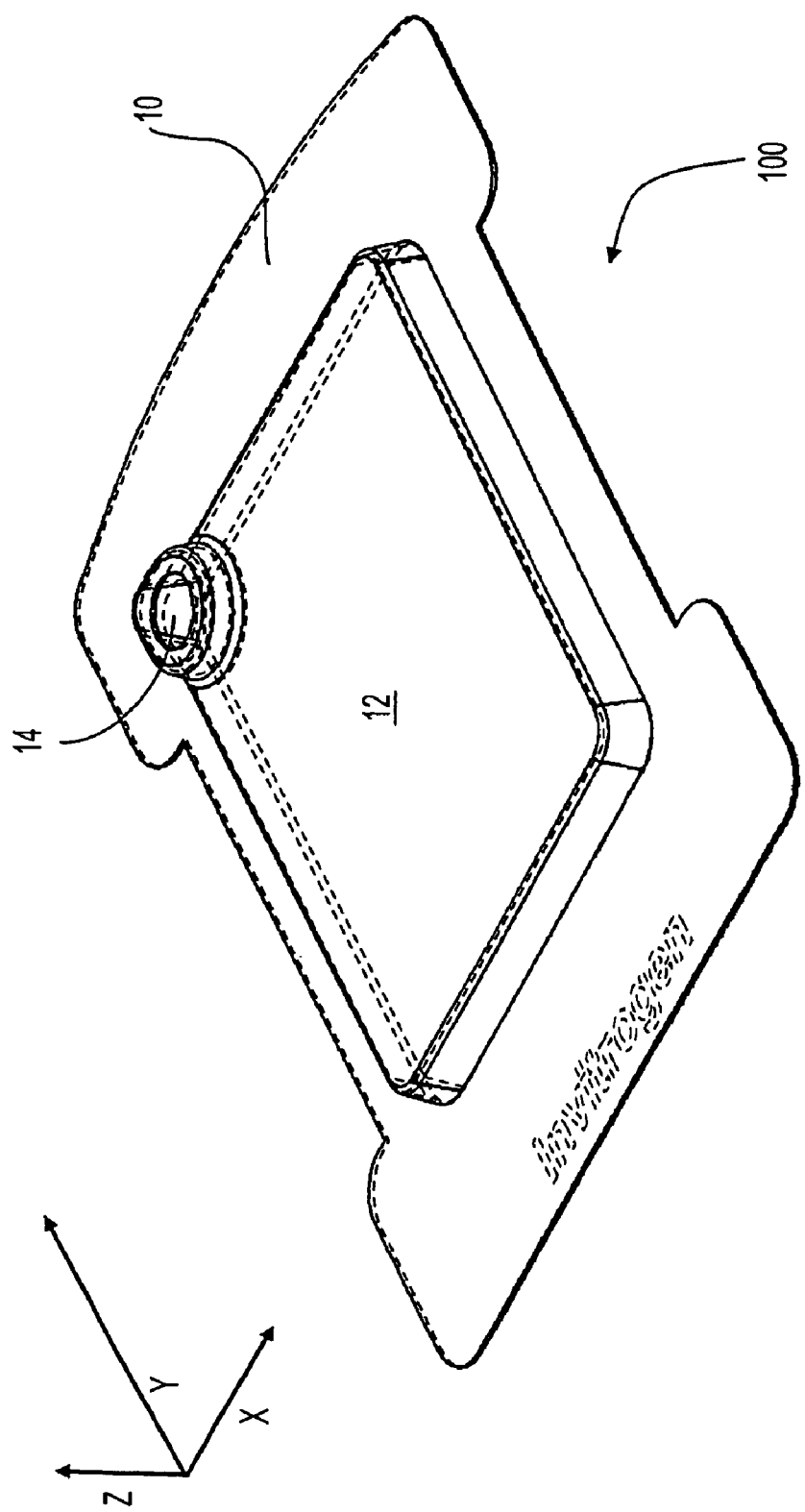
FIG. 4 is an isometric view of the second (cassette-distal) face of a chamber-forming electrophoresis cassette cover of the present invention.

With reference to FIG. 4, cover 100 comprises cassette-contacting member 10 and at least one chamber-defining member 12.

In the embodiment shown in FIG. 4, cover 100 comprises only a single chamber-defining member. In other embodiments, such as that shown in FIG. 14, cover 100 comprises a plurality of chamber-defining members 12.

Figure 5:
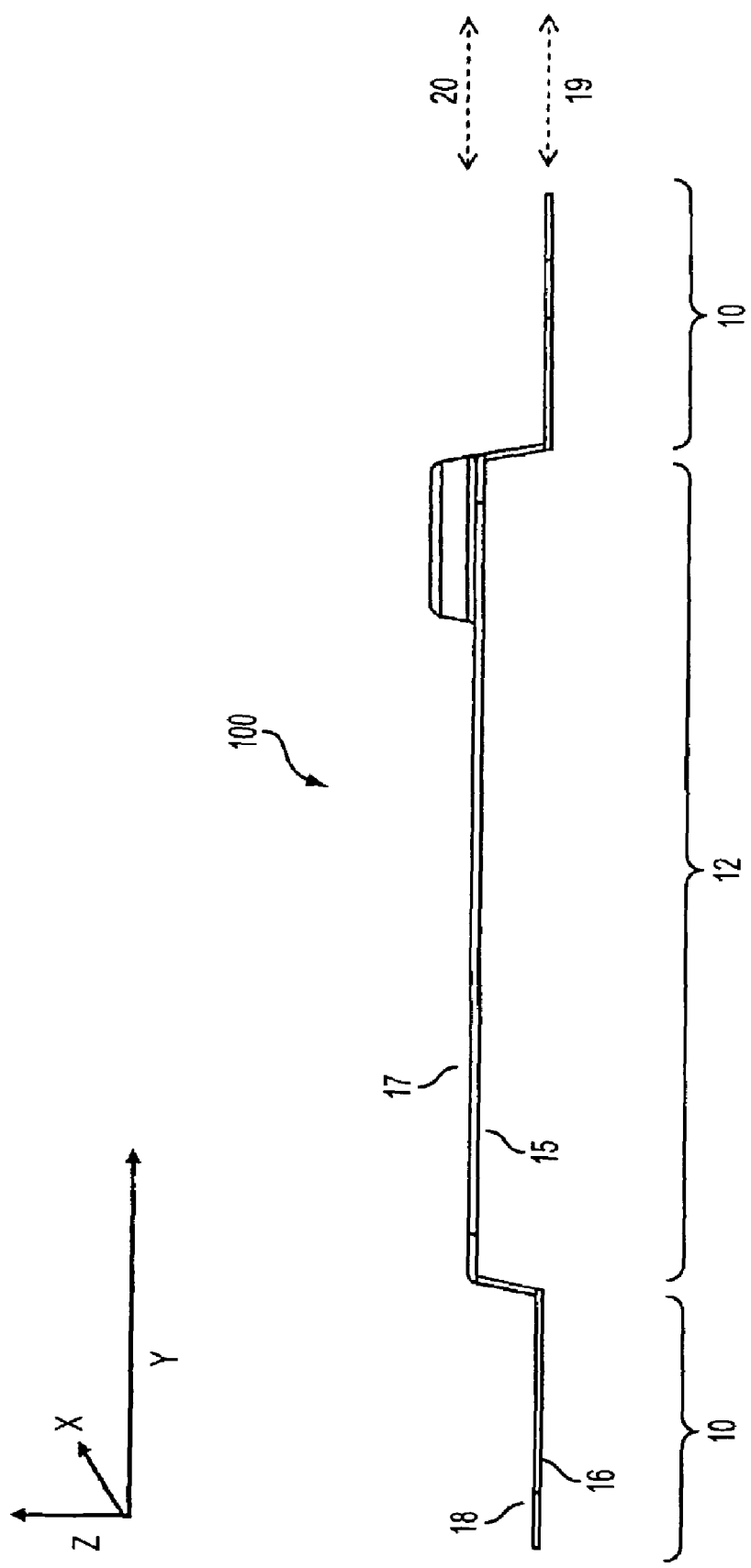
FIG. 5 is a side view of the embodiment shown in FIG. 4.

With reference to a side view of the embodiment of FIG. 4, shown in FIG. 5, first face 16 of cassette-contacting member 10 is in surface continuity with first face 15 of each chamber-defining member 12; the continuous surface defines a first face of cover 100. The first face of cover 100 is the cassette-proximal—i.e., cassette-contacting—face of cover 100. Second face 18 of cassette-contacting member 10 is in surface continuity with second face 17 of chamber-defining member 12; the continuous surface defines a second face of cover 100. The second face of cover 100 is the cassette-distal face of cover 100.

Cassette-contacting member 10 is disposed circumferentially around each chamber-defining member 12 of cover 100 at first elevation 19 (see FIG. 5). Each chamber-defining member elevates the cover's first face in the direction of the cover's second face (direction "Z" in FIGS. 4 and 5) to at least second cover elevation 20 (FIG. 5). Typically, the chamber defining member equally elevates both the cover's first and second face, thus maintaining a substantially uniform thickness throughout chamber-defining member 12.

Figure 6:
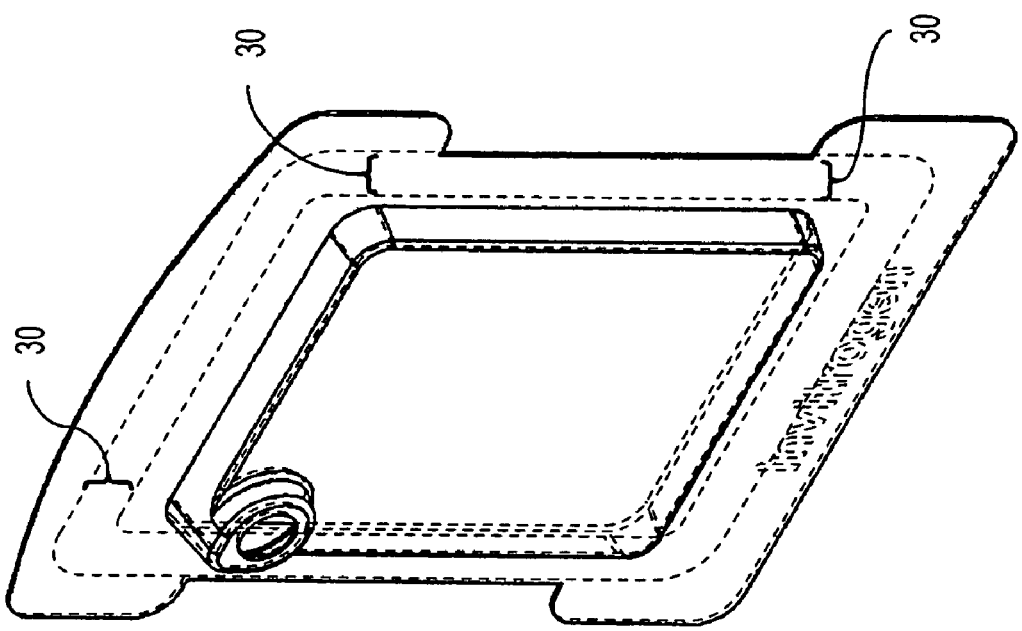
FIG. 6 is a perspective view of the second (cassette-distal) face of the chamber-forming electrophoresis cover of the present invention, further showing the location (in phantom outline) of sealing means disposed on the first (cassette-proximal) face of the cassette-contacting member of the cover.

Cover 100 further comprises sealing means 30, disposed circumferentially around each chamber-defining member 12 on first face 16 (i.e., on the cassette-contacting, cassette-proximal face) of cassette-contacting member 10, as shown in outline in FIG. 6, a perspective view of the second (i.e., cassette-distal) face of an embodiment of cover 100.

Typically, each chamber-defining member additionally comprises at least one fluid port 14. Fluid port 14 includes a through bore which traverses both the first and second faces of the chamber-defining member, permitting fluids— such as buffers containing reducing and alkylating agents— to be introduced into the chamber, and thus into fluid communication with a face of cassette 200.

Figure 9:
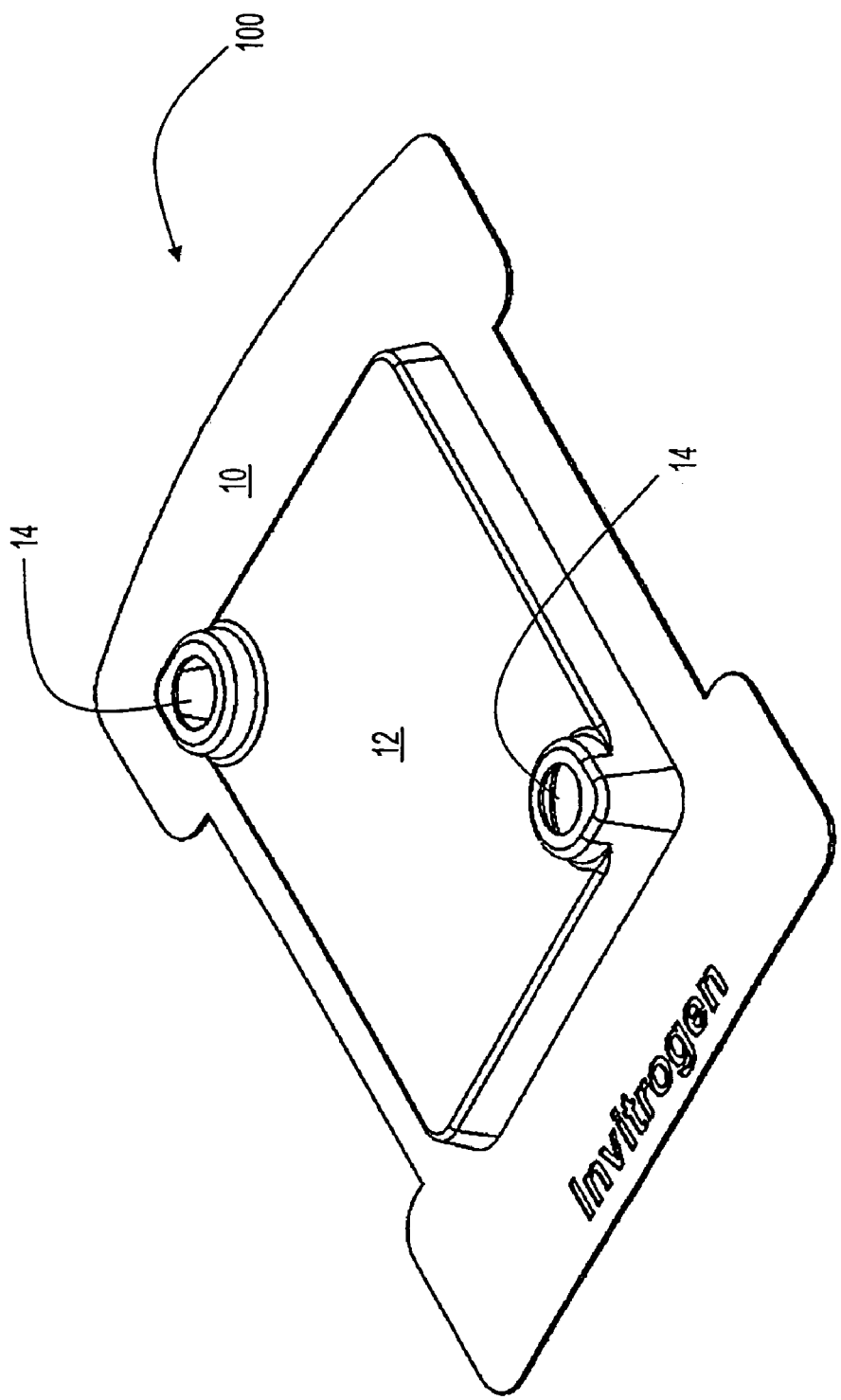
FIG. 9 is an isometric view of the second (cassette-distal) face of an embodiment of the cover of the present invention in which a single chamber-defining element has two fluid ports.
Figure 10:
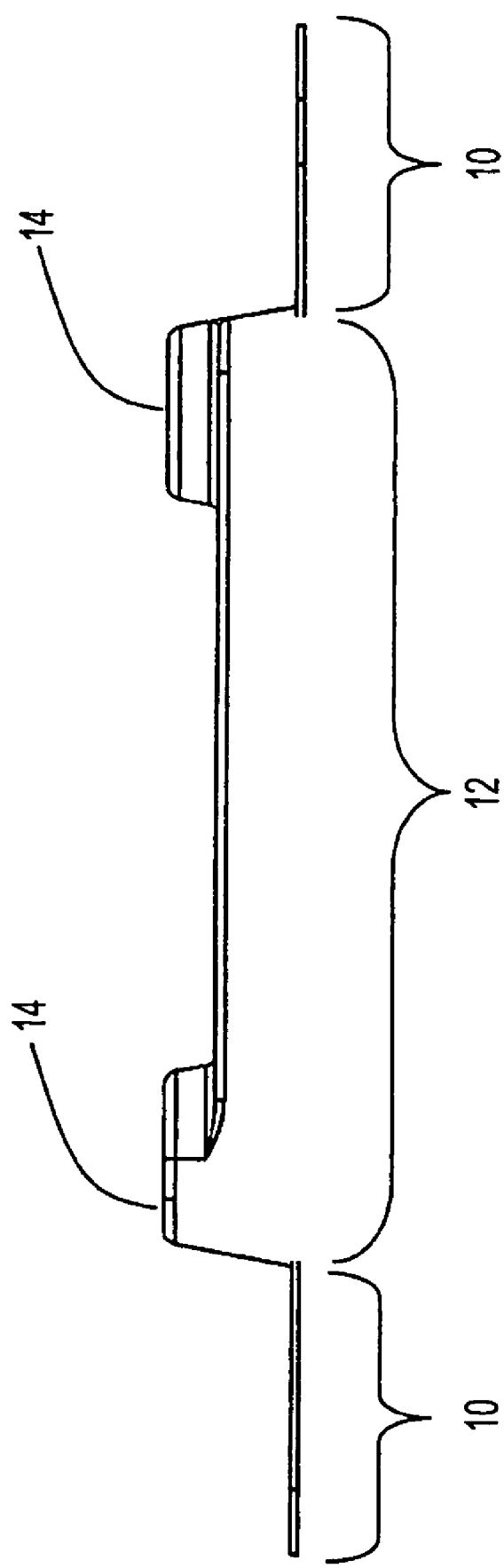
FIG. 10 is a side view of the embodiment shown in FIG. 9.
Figure 11:
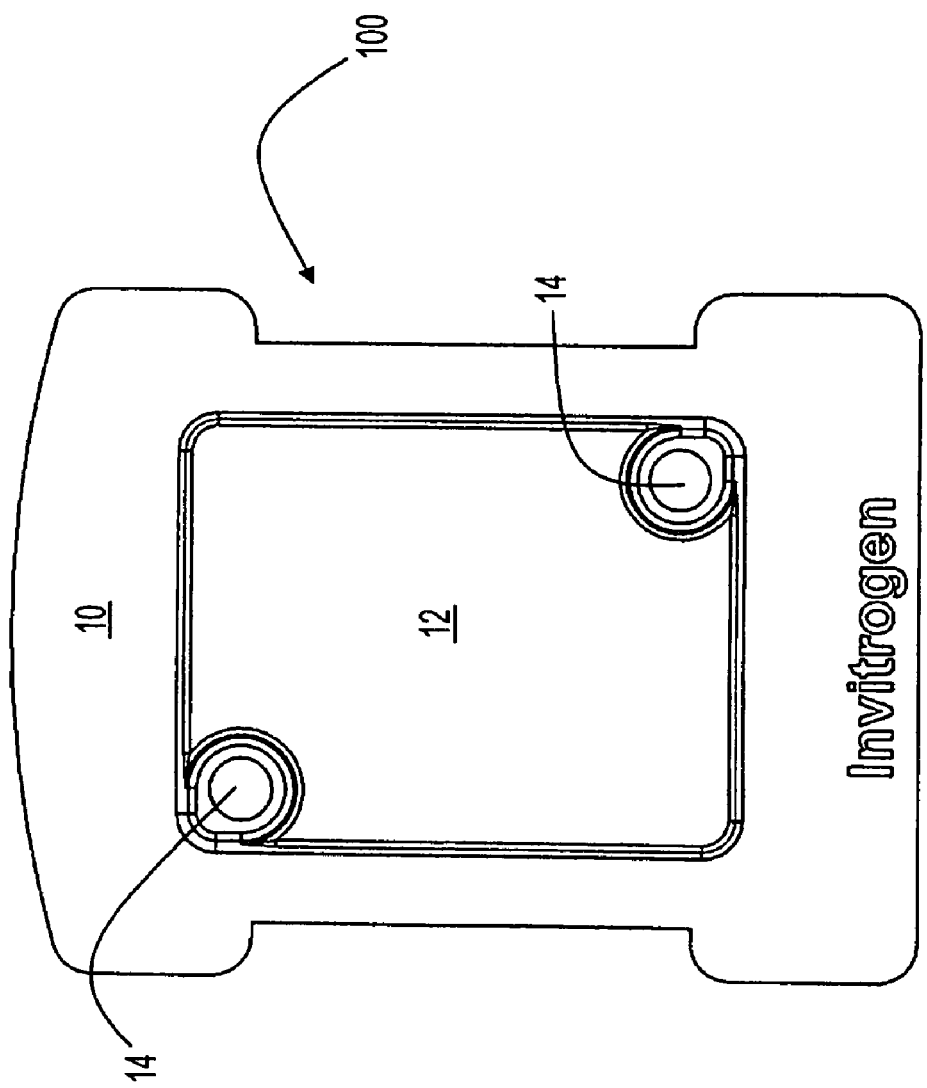
FIG. 11 shows the embodiment of the cover shown in FIGS. 9 and 10, viewed from the second (cassette-distal) face of the cover.
Figure 14:
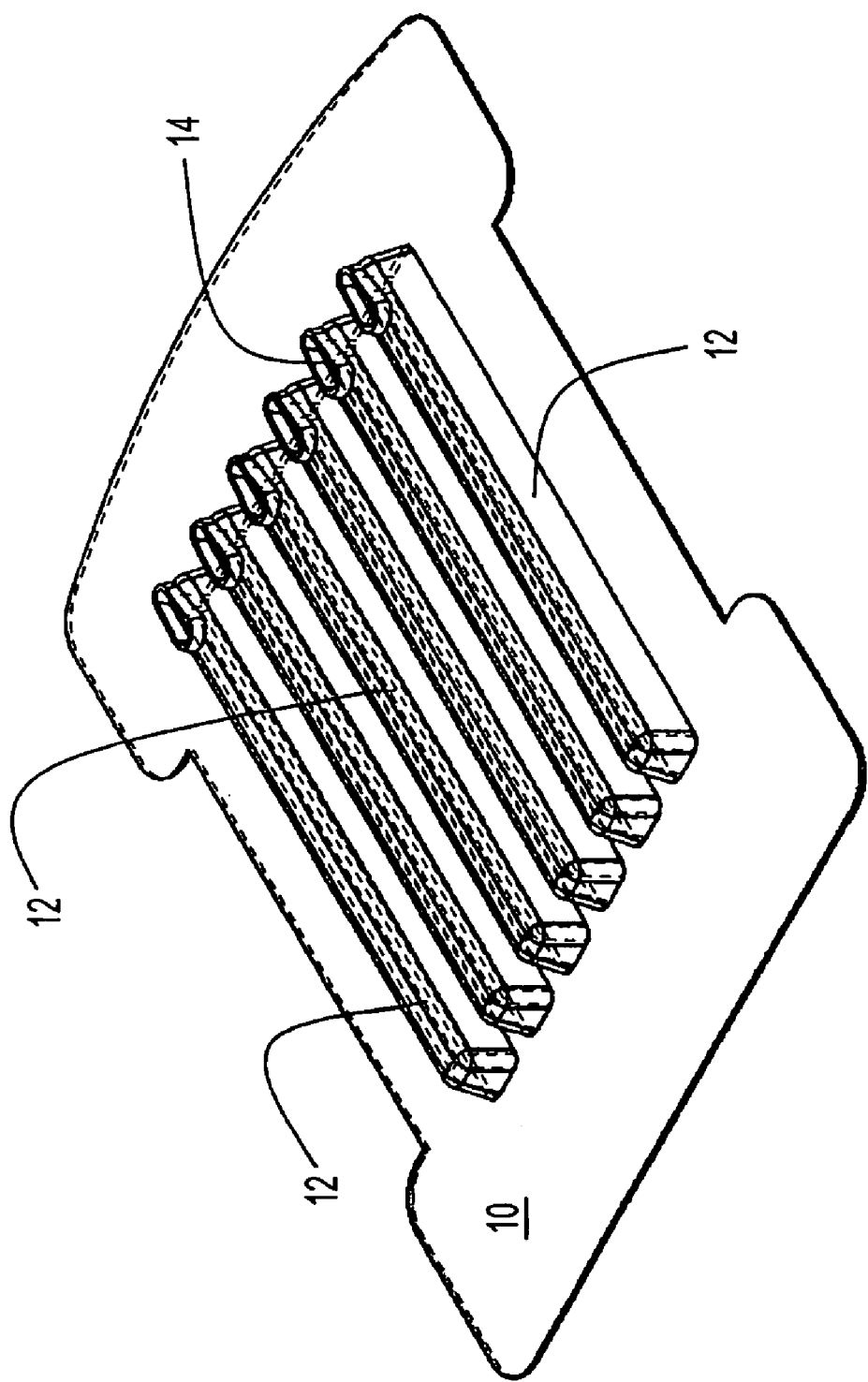
FIG. 14 is an isometric view of an embodiment of the cover of the present invention having six chamber-defining elements, each with a single fluid port.

In some embodiments, such as those shown in FIGS. 4 and 14, each chamber-defining element 12 has a single fluid port 14. In other embodiments, however, each chamber-defining element has a plurality of fluid ports. In the embodiments shown in FIGS. 9–11, for example, singular chamber-defining element 12 has two fluid ports 14. The additional ports usefully act as vents, facilitating the filling and decantation of fluids from the assembled chamber.

Figure 12:
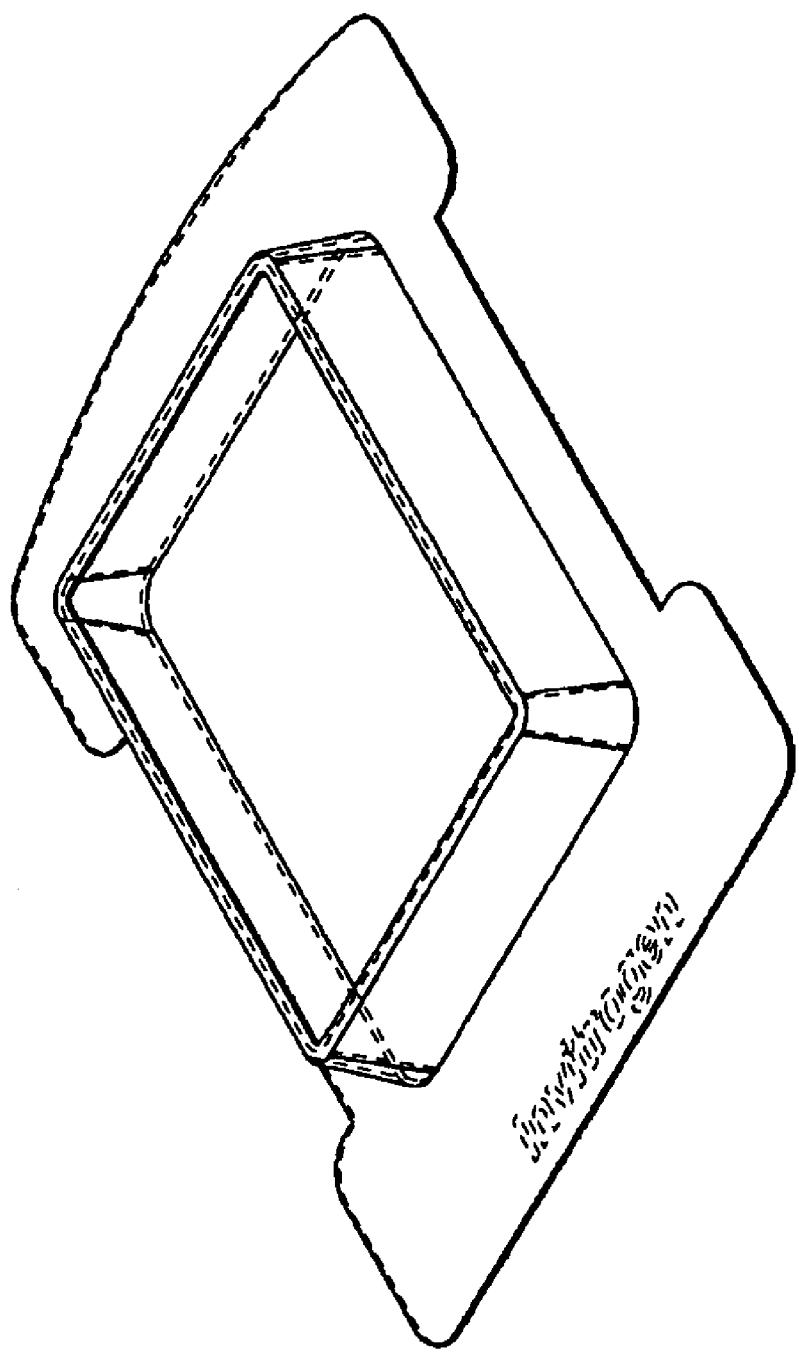
FIG. 12 is an isometric view of an embodiment of the cover of the present invention in which the fluid port occupies a substantial part of the chamber-defining element.
Figure 13:
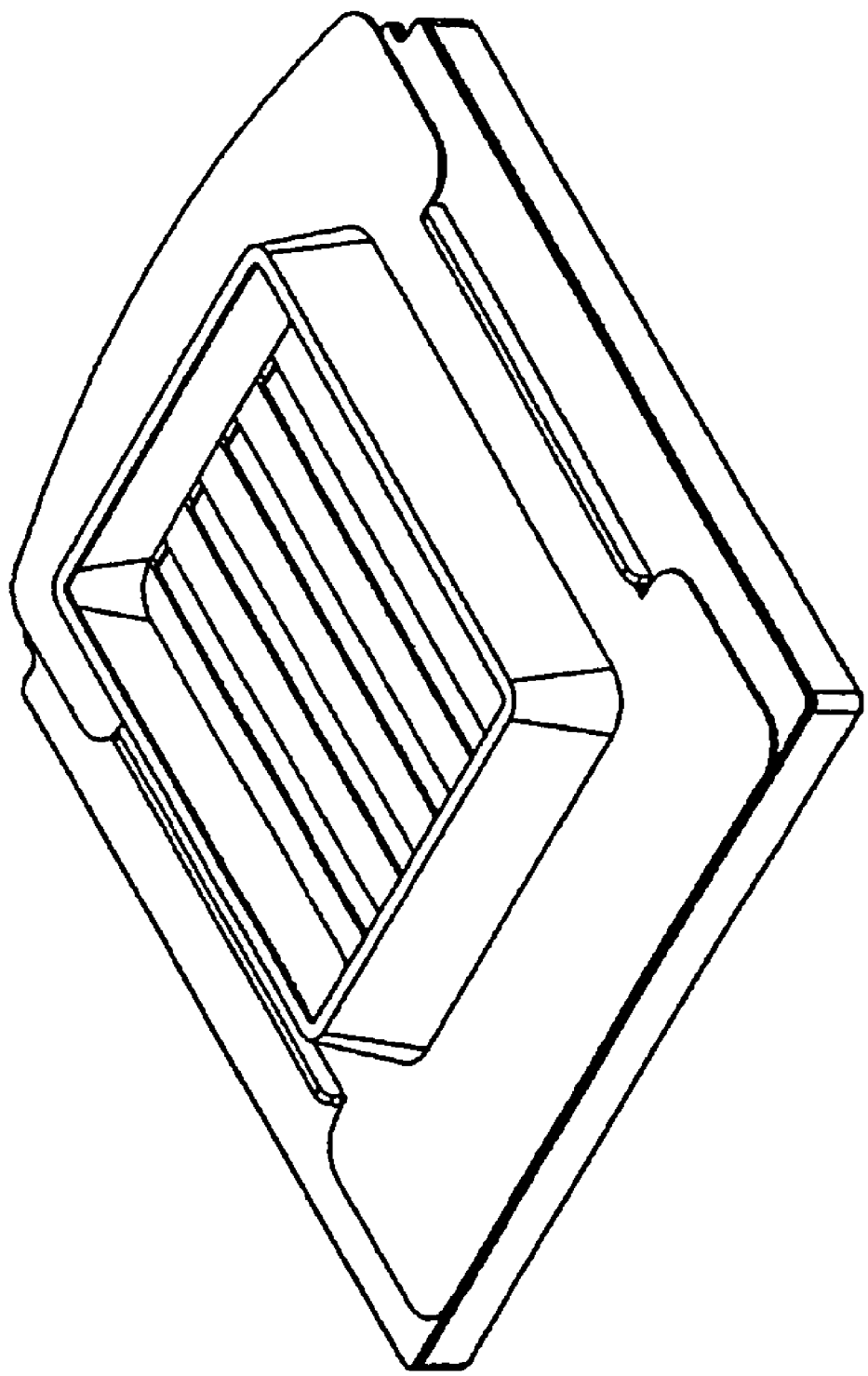
FIG. 13 is an isometric view of the cover shown in FIG. 12, operationally assembled to a face of an electrophoresis cassette having a plurality of channels exposed to the interior of the assembled chamber.

In a further embodiment, illustrated in FIG. 12, the fluid port occupies a substantial portion of the chamber-defining element. FIG. 13 is an isometric view of the embodiment of FIG. 12 operationally assembled to an electrophoresis cassette having a plurality of channels exposed to the interior of the assembled chamber.

In one series of embodiments, cassette-contacting member 10 and chamber-defining member 12 of cassette cover 100 are of integral manufacture, typically molded as a single piece.

Single piece molded covers 100 are usefully constructed of plastic, such as a thermoformable plastic, such as polypropylene, polyethylene, or PVC. In other such embodiments, the cover is injection molded, and constructed from a plastic such as polycarbonate, polystyrene, acrylic, ABS, polyvinylchloride, polypropylene, polyethylene or plasticized alloys thereof.

After molding, the cover can be further shaped by milling, cutting or trimming, or other techniques well known in the art.

In other embodiments, cassette-contacting member 10 and chamber-defining member 12 of cassette cover 100 are manufactured as separate parts which are thereafter attached to one another with fluid-proof seams.

Sealing means 30 must be capable of creating a fluid-tight seal between the first face (i.e., cassette-contacting, cassette-proximal face) of cover 100 and a face of cassette 200 without leaching contaminants into the fluid intended to be retained within the assembled chamber. Usefully, sealing means 30 permits the reversible assembly of cover 100 to cassette 200, allowing the chamber so formed to be disassembled after suitable periods of contact of the face of cassette 200 to fluid retained within the assembled chamber.

In one series of embodiments, sealing means 30 includes an adhesive layer.

The adhesive layer can include any water-insoluble adhesive that does not leach detectable contaminants into the solution.

Such adhesives include, for example, acrylic adhesives, such as an acrylic adhesive disposed on both sides of a polyethylene or polyvinylchloride tape. Such tapes are available commercially and include, for example, 3M™ 9690, a polyester film carrier coated on both sides with a high strength 300 MP acrylic adhesive (3M, Minneapolis, Minn., USA).

In use, sealing means 30 is used sealingly to engage cover 100 to cassette 200, creating one or more fluid-retaining chambers on a face of an electrophoresis cassette. The face of the electrophoresis cassette contributes a wall to the fluid-retaining chamber, thus placing the cassette face in fluid communication with the contents of the chamber.

Figure 7:
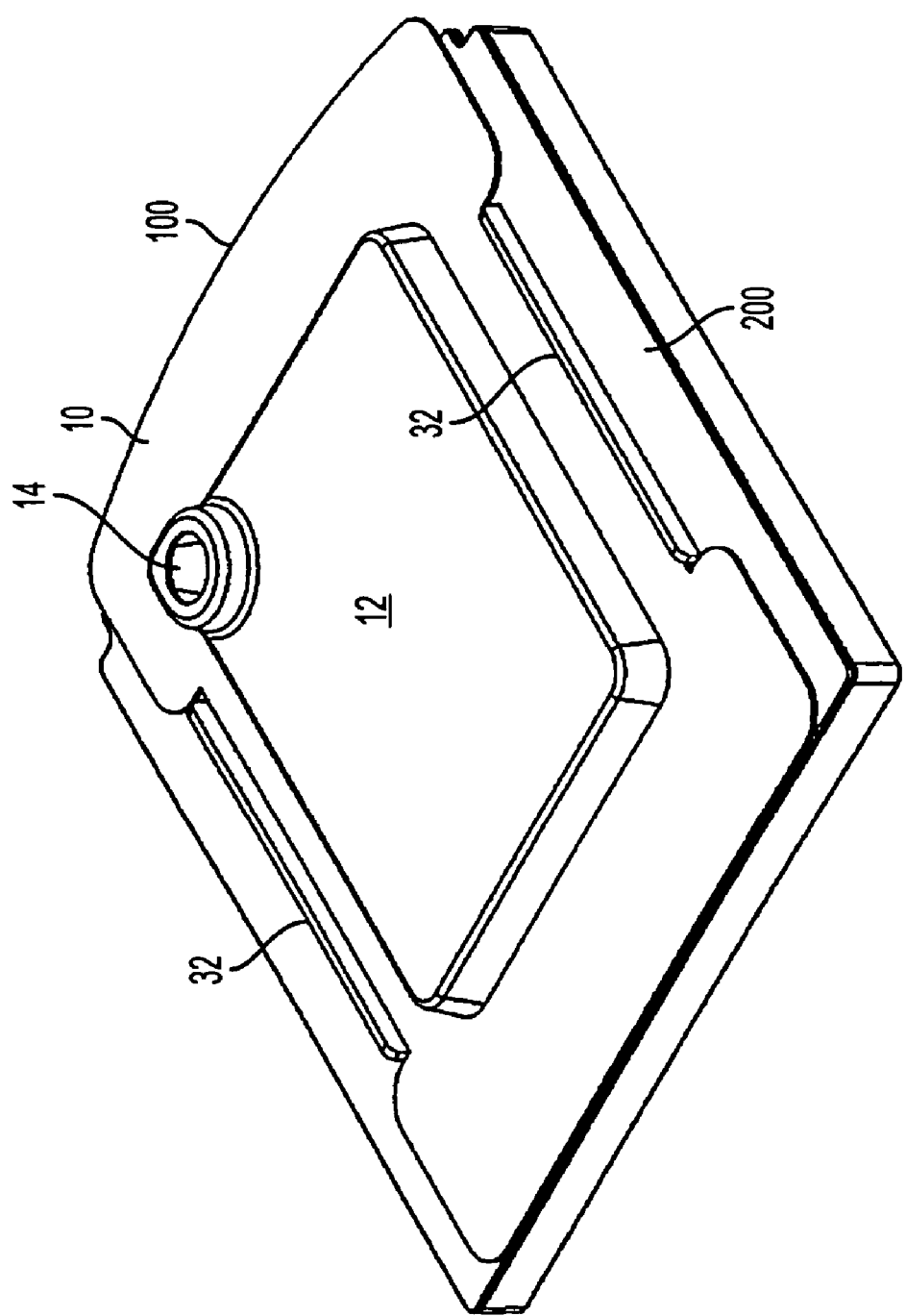
FIG. 7 is an isometric view of the second (cassette-distal) face of a cover of the present invention, operationally assembled on a face of an electrophoresis cassette to form a chamber thereupon.

FIGS. 7 and 13 are isometric views of different embodiments of cover 100 sealingly engaged to cassette 200, as viewed above the second face of cover 100. In the embodiment shown in FIG. 7, cover 100 has a single chamber-defining member 12 with a single fluid port 14. In the embodiment shown in FIG. 13, the single fluid port occupies a substantial portion of the chamber-defining element.

The cassette illustrated in FIGS. 7 and 13 is an IPGRunner™ cassette (Invitrogen Corp., Carlsbad, Calif., USA). As further described below, the chamber-forming electrophoresis cassette cover of the present invention finds particular utility in facilitating the reduction, alkylation, and equilibration of protein analytes that have been focused in immobilized pH gradient (IPG) strips within IPGRunner™ cassettes.

However, it should be understood that the chamber-forming electrophoresis cassette cover of the present invention can also be used with other types of cassettes, and to methods other than isoelectric focusing in IPG strips.

For example, the chamber-forming cover (synonymously, "tray") of the present invention can be sealingly engaged to an electrophoresis cassette that is adapted to performing other types of first dimension separation, such as nondenaturing gel electrophoresis, either before or after such first dimension separation.

If used before such electrophoretic separation, the chamber-forming tray of the present invention can be used, e.g., to facilitate rehydration of a gel, such as a rehydratable pre-cast nondenaturing electrophoresis gel, to equilibrate a gel with desired buffers, to impregnate the gel with real-time detection agents, such as biarsenical fluors capable of binding tetracysteine-tagged proteins, or introduce soluble ampholytes for isoelectric focusing.

If used after such first dimension electrophoretic separation, the chamber-forming cover of the present invention can usefully facilitate staining of analytes within the gel, or exposure of the analytes to reducing and/or alkylating agents, or exposure of the analytes to chaotropes, or to equilibrate the gel with any desired compound prior to analysis or a second dimension separation.

Analogously, the chamber-forming tray of the present invention can be used with a variety of cassettes adapted to performing other types of second dimension separation, such as nondenaturing gel electrophoresis, or a second dimension of isoelectric focusing, either before or after such second dimension separation.

FIGS. 7 and 13 further illustrate that cassette-contacting member 10 of cassette 100 can usefully conform in shape to cassette 200, the conformal shape facilitating alignment during assembly.

In the embodiments shown, for example, the outer dimensions of cover 100 approximate those of cassette 200. The dimensions need not be identical, however: as shown, cassette-contacting member 10 of cover 100 is usefully shaped to overshoot at least one side of cassette 200, creating a leverage-yielding portion of cassette-contacting element 10 that facilitates the manual separation of cover 100 from cassette 200 after use of the chamber. As also shown, cassette-contacting member 10 of cover 100 is shaped to snug to and between ribs 32 of IPGRunner™ cassette 200.

Figure 8:
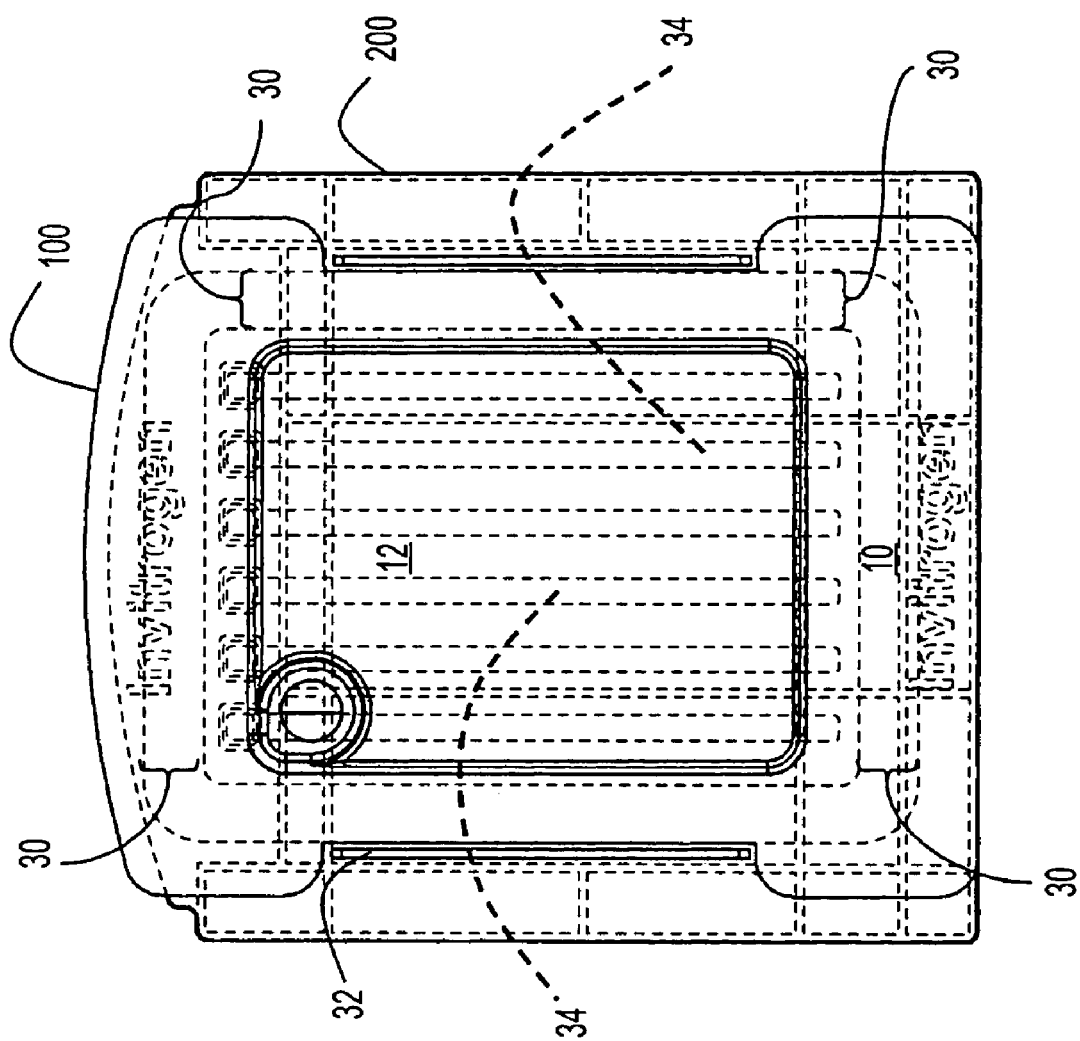
FIG. 8 is a view of the assembly of FIG. 7, viewed from the second (cassette-distal) face of the cover of the present invention, with both cover and cassette rendered as transparent.

FIG. 8 is a top view of the assembly of FIG. 7, viewed from the second (i.e., cassette-distal) face of the cover of the present invention.

Both cover 100 and cassette 200 are rendered as transparent in FIG. 8: although not necessary, cover 100 is usefully manufactured of transparent or translucent material, facilitating visualization of the cassette after assembly of cover 100 thereon; although not necessary, the commercially available IPGRunner™ cassette is transparent as sold.

In the embodiment shown, cassette 200 has six channels 34 within each of which a single IPG strip may be resident during isoelectric focusing. As further described below, cover 100 of the present invention is typically assembled to such cassettes after isoelectric focusing has been completed, with focused IPG strips resident within one or more of channels 34. But as additionally described below, in embodiments in which the cassette so permits, cover 100 of the present invention can be assembled to such cassette before a first dimension separation.

In the embodiment shown in FIG. 8, cassette-contacting member 10 of cover 100 is usefully further dimensioned to overlie the top and bottom of plural channels 34; in contrast, sealing means 30 is disposed so that it does not overlie any portion of channels 34. In such embodiments, cassette-contacting member 10 of cover 100 usefully acts to retain IPG strips within channels 34 after sealing engagement of the cover to the cassette without, however, disadvantageously exposing the IPG strips to adhesive present on sealing means 30. As a result, IPG strips resident in channels 34 of cassette 200 do not float free when exposed to fluid retained within the assembled chamber.

FIG. 14 shows an embodiment of the cover of the present invention having plural chamber-defining elements 12. Each chamber-defining element 12 is circumferentially bounded by cassette-contacting element 10 and, although not shown, by sealing means 30, thus creating a plurality of fluidly noncommunicating chambers upon assembly to cassette 200.

Such plural chamber defining elements—and upon assembly, corresponding plural fluid-retaining chambers—of which there can be 2, 3, 4, 5, 6, 7, 8, 9, or 10 or more, can usefully be positioned so that each such chamber overlies a separate portion of cassette 200. In embodiments of cassette 200 having plural channels, such as that illustrated in FIG. 8, each such chamber can usefully be positioned to overlie a single channel of cassette 200, permitting each channel to be discretely and separately contacted to a discrete fluid, reducing opportunities for cross-contamination and optionally permitting different fluids, such as different buffers, to be used.

The internal volume of each chamber formed by assembly of a cover of the present invention to an electrophoresis cassette will depend primarily upon the dimensions of chamber-defining member 12, including the extent of differential elevation (or elevations) between circumferential cassette-contacting member 10 and chamber-defining member 12, although depressions, channels, or chambers formed within cassette 200 may further contribute to the volume of the assembled chamber.

Typically, such chambers are capable of retaining at least 1 ml of fluid, 2 ml, 3 ml, 4 ml, even 5 ml or more, with intermediate volumes permissible. Particularly in embodiments in which a single chamber-defining element 12 is present in cover 100, chamber-defining element 12 can be dimensioned to provide a chamber capable of retaining at least 6 ml, 7 ml, 8 ml, 9 ml, 10 ml, 11 ml, 12 ml, 13 ml, 14 ml, even 15 ml, 16 ml, 17 ml, 18 ml, 19 ml, or even 20 ml or more, with intermediate volumes permissible.

The volume desired to be retained within the chamber will typically be a volume sufficient to provide adequate equilibration of gels present within or upon cassette 200, without inconvenient wastage of reagents.

In a second aspect, the invention provides methods for contacting a gel present within or upon an electrophoresis cassette with a fluid volume.

Typically, in a first step of such method, the gel immobilized within or upon the cassette is exposed, i.e., brought into fluid communication with a first (that is, cover-proximal, cover-contacting) face of the cassette.

Figure 1:
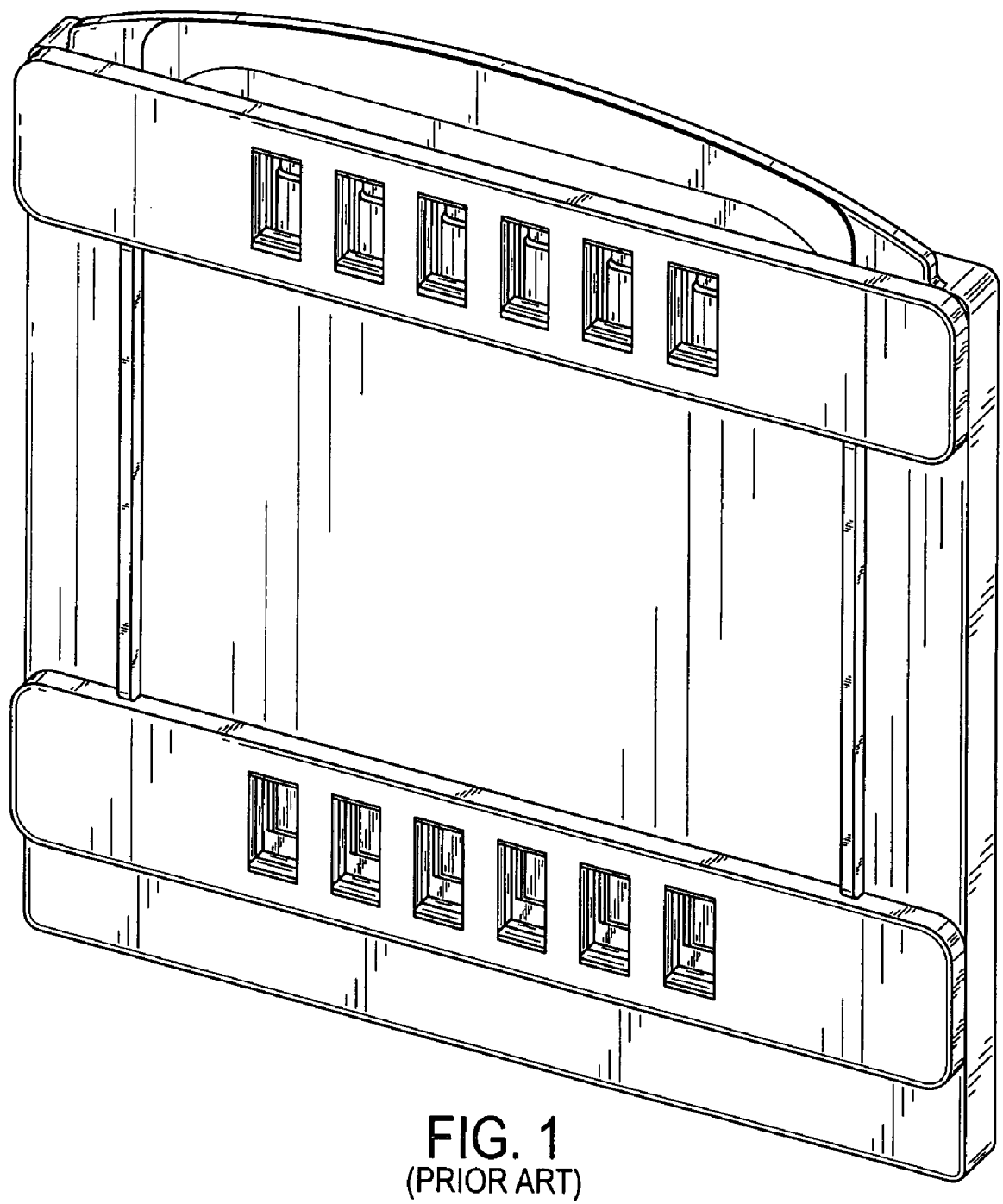
FIG. 1 is a front perspective view of a prior art electrophoresis cassette that is particularly adapted for rapid, parallel, isoelectric focusing of analytes on immobilized pH gradient (IPG) strips, prior to use.
Figure 2:
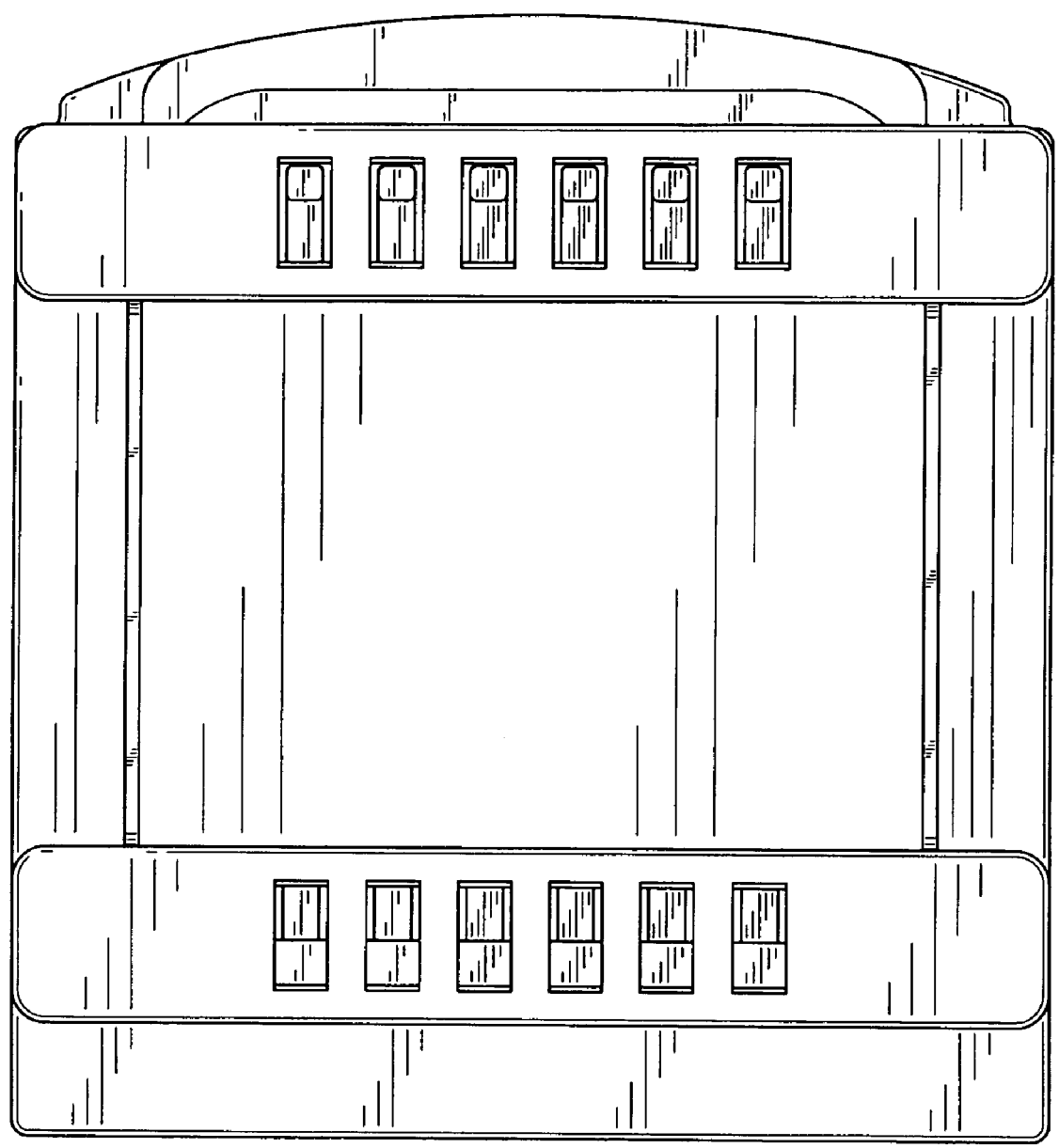
FIG. 2 is a front perspective view of the cassette of FIG. 1, prior to use.

FIGS. 1 and 2 show an exemplary electrophoresis cassette of the prior art, prior to use. The cassette shown, which is further described in commonly owned U.S. patent application publication No. 2003/0015426 and international patent publication no. WO 02/092200, the disclosures of which are incorporated herein by reference in their entireties, an embodiment of which is available commercially as the IPGRunner™ (Invitrogen Corp., Carlsbad, Calif.), permits first dimension isoelectric focusing of IPG strips within internal channels that permit spaced electrical communication with the enclosed strips.

Figure 3:
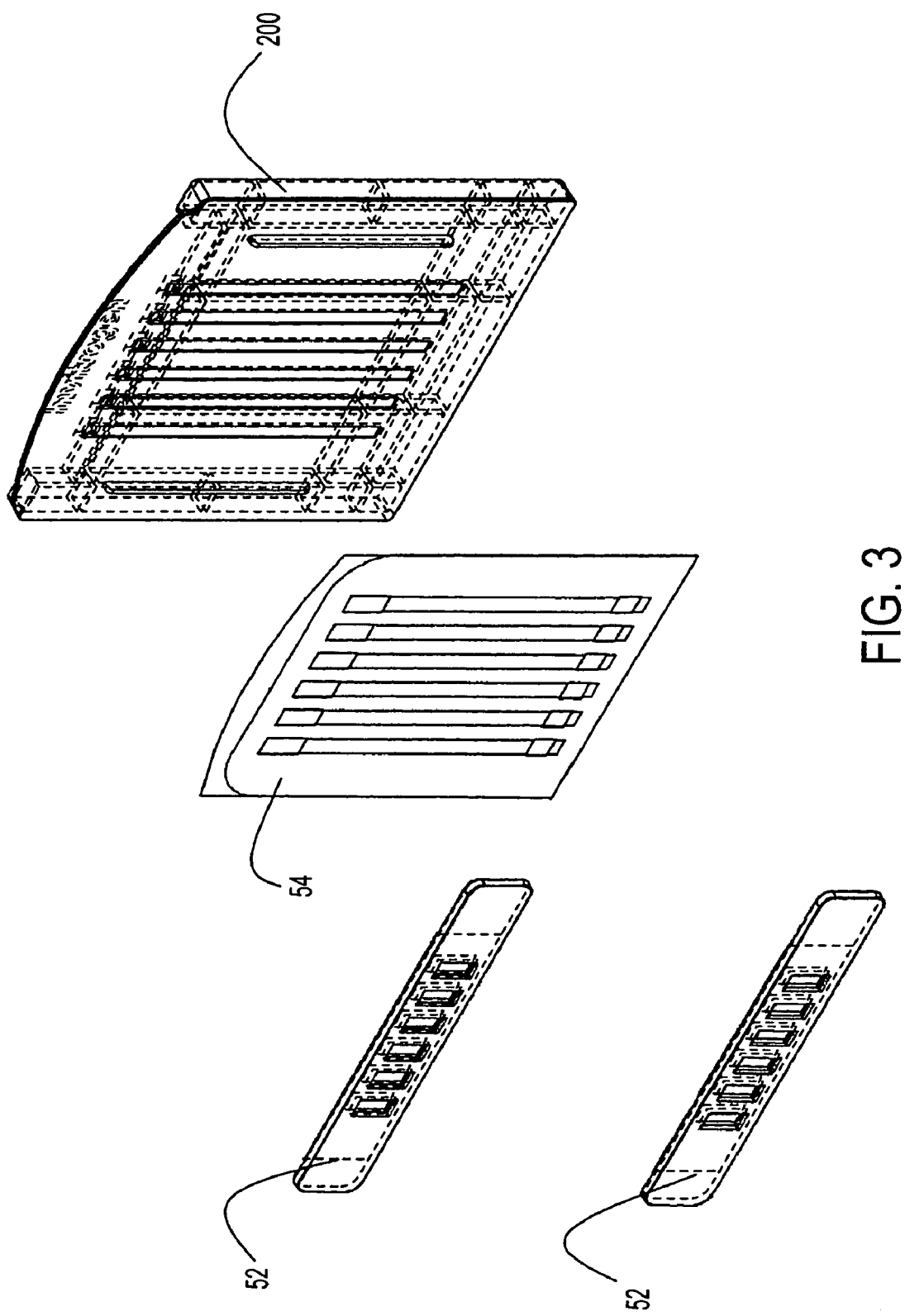
FIG. 3 is an exploded front perspective view of the cassette of FIGS. 1 and 2, demonstrating parts that are removed from the cassette in order to expose the interior channels of the cassette upon completion of focusing; IPG strips resident within the channels are not shown.

The entire longitudinal length of the channels, and thus the entire longitudinal length of the strips resident therein, is exposed in two steps, shown in the exploded view of FIG. 3: well forming members 52 are removed after rehydration of the strips and prior to focusing; laminar film cover 54 is removed after focusing.

Cover 100 is then sealingly assembled to cassette 200, with the first (cassette-contacting) face of cover 100 contacting the first (cover-contacting) face of cassette 200, creating one or more fluid-retaining chambers thereupon.

A desired fluid is then introduced into the chamber, whereupon it contacts the first face of cassette 200 and gels that are in fluid communication therewith. In embodiments in which chamber-defining elements of cover 100 have one or more fluid ports, fluid is introduced through the fluid ports.

Fluid port 14 may optionally be configured to accept a sealing plug (not shown). In such cases, the chamber may be plugged and the assembled cassette and cover incubated in any orientation. More typically, however, the fluid port is left unplugged, in which case the assemblage is advantageously positioned horizontally with fluid ports superior, allowing fluid to be retained within the chamber (or plural chambers) by gravity alone.

The fluid solution may, for example, be a staining or destaining solution, useful for visualizing analytes within the gel, or may be a solution containing one or more natural or artificial enzyme substrates.

When the gel is part of an IPG strip, the fluid may, alternatively or in addition, advantageously contain detergent, reducing agents, and/or alkylating agents to prepare the strips for the second dimension separation.

For example, the chamber may be filled with a first buffer containing reducing agents, such as dithiothreitol (DTT), optionally with additional conditioning or surface active agents such as glycerol, buffering agents, such as Tris, one or more detergents, such as lithium or sodium dodecylsulfate, one or more chelating agents, such as EDTA, and one or more dyes or indicators, such as Serva Blue G-250 dye and phenol red.

After a suitable incubation, such as 5 minutes, 10 minutes, 15 minutes, 20 minutes, 25 minutes, even 30 minutes or more, with intermediate values permissible, the fluid is removed, such as by decantation through fluid ports 14.

In some embodiments of the methods of the present invention, the filling, incubating, and fluid removal steps may optionally be iterated, either with fluid identical in composition to that used in earlier steps or with fluids of different composition.

For example, in embodiments in which the gel is part of an IPG strip and the first fluid contains reducing agents, a subsequent fluid may usefully contain alkylating agents, such as iodoacetamide, optionally with additional conditioning or surface active agents such as glycerol, buffering agents, such as Tris, one or more detergents, such as lithium dodecylsulfate, one or more chelating agents, such as EDTA, and one or more dyes or indicators, such as Serva Blue G-250 dye and phenol red. As is known in the art, alkylating the sulfhydryl groups of proteins reduces vertical streaking of protein bands during 2D electrophoresis.

After a suitable incubation, such as 5 minutes, 10 minutes, 15 minutes, 20 minutes, 25 minutes, even 30 minutes or more, with intermediate values permissible, the fluid is removed, as by decantation through fluid ports 14.

The steps of fluid introduction, incubation, and fluid removal—as by decantation—may be further iterated.

Following fluid contact to the gel, whether a single fluid or succession of fluids, whether of identical or disparate compositions, the cover is usefully removed and the gel thereafter subjected to various analytical procedures known in the art.

For example, in embodiments of the methods of the present invention in which the gel is part of an IPG strip, the strip can be contacted to a second gel for second dimension size separation. The second gel can usefully, for example, be a 4–12% Bis-Tris ZOOM® Gel or a Novex 4–20% Tris-Glycine ZOOM® Gel (both available from Invitrogen Corp., Carlsbad, Calif., USA).

Figure 15:
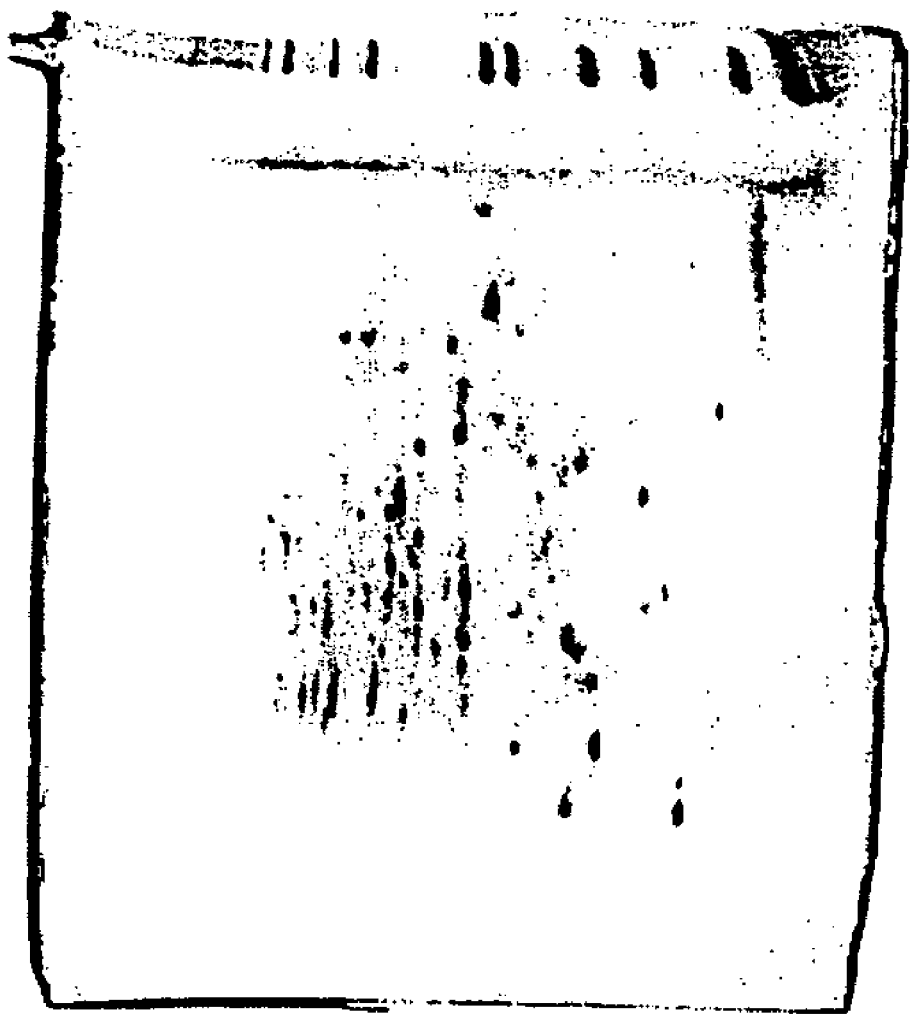
FIG. 15 is a scanned image of a stained gel obtained by two-dimensional polyacrylamide gel electrophoresis (2D-PAGE) of an *E. coli* lysate, in which first dimension isoelectric focusing was performed on an IPG strip within an electrophoresis cassette of FIGS. 1–3, reduction and alkylation of proteins within the focused IPG strips was performed using fluids retained within a chamber assembled on the cassette using a cover of the present invention, and in which second dimension size separation was performed by standard techniques.
Figure 16:
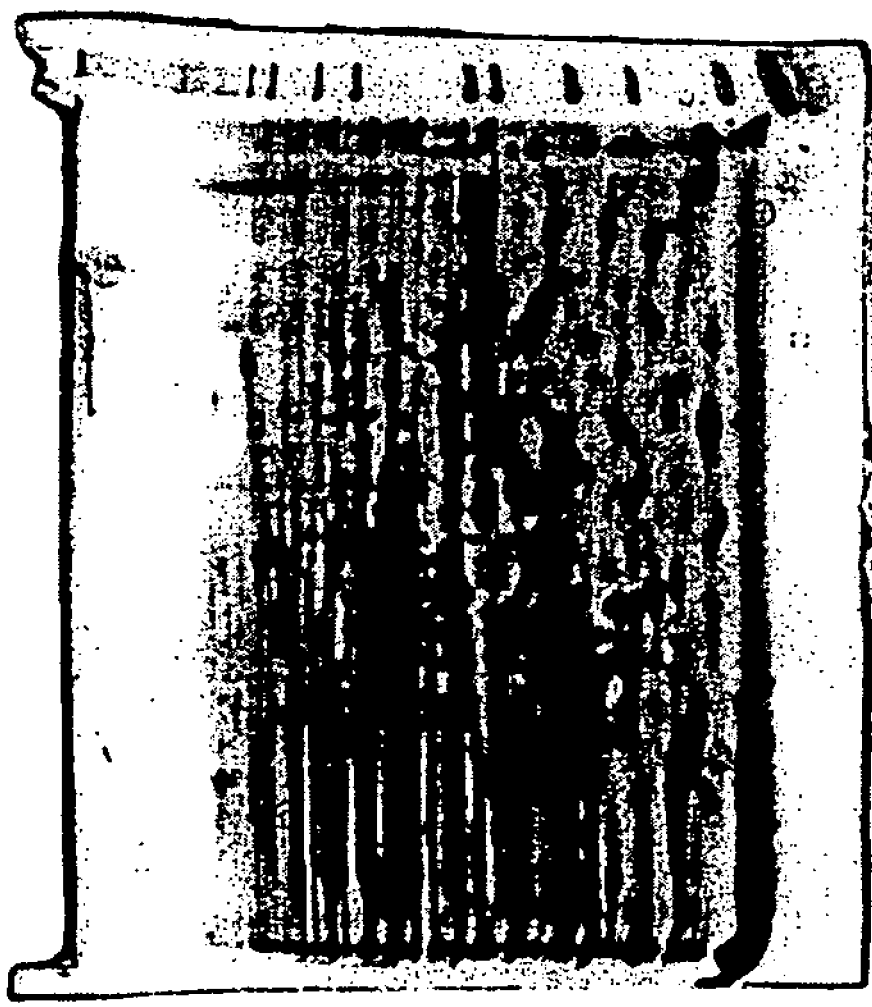
FIG. 16 is a scanned image of a stained gel obtained as in FIG. 15, with excessive amounts of *E. coli* lysate.

FIGS. 15 and 16 are scanned images of stained gels, each obtained by two-dimensional polyacrylamide gel electrophoresis (2D-PAGE) of an *E. coli* lysate in which first dimension isoelectric focusing was performed on an IPG strip within an IPGRunner cassette (Invitrogen Corp., Carlsbad, Calif., USA).

To obtain these images, following removal of the laminar film cover, the IPGRunner cassette with IPG strips resident within the exposed cassette channels was assembled to a chamber-forming cover of the present invention. Reduction and alkylation of proteins within the focused IPG strips was performed by contact to successive buffers retained within the assembled chamber. The final buffer was decanted, the cover removed, and second dimension separation performed according to standard techniques.

As can be seen, even with the intentional overloading of the gel shown in FIG. 16, there is no significant vertical streaking, indicating successful reduction and alkylation of the proteins using the chamber-forming cover of the present invention.

Other experiments, not shown, indicate that a cover having an adhesive layer of 3M 9690 tape is capable of producing a detachable seal that remains liquid-tight for weeks in the presence of equilibration buffer, and that during these extended incubations there is no detectable leaching of contaminants into the buffer from either the adhesive or the cover.

Further experiments, also not shown, demonstrate that there is no significant protein cross-contamination among IPG strips present within parallel channels of an IPGRunner™ cassette when a cover is used that has a single chamber-defining member, thus placing all of the IPG strips in fluid communication with one another during the equilibration step.

As noted above, in other embodiments of the methods of the present invention, cassettes analogous to but differing from the IPGRunner™ cassette, can be used. For example, in some embodiments, the cassette may have a laminar cover that is reversibly attachable and removable from the cassette. Such cassettes permit the chamber-forming tray of the present invention to be attached prior to electrophoretic separation, permitting gels or gel strips present therein or thereupon to be contacted to a fluid that usefully facilitates separation and/or analysis. In yet other embodiments, the cassette may have an attachable laminar cover that is provided disattached from the cassette, for example bundled in a kit with such cassette, to be attached subsequent to use of the chamber-forming tray of the present invention. In some of these embodiments, the cassette can be provided with one or more gels or gel strips already present therein or thereupon.

In a further aspect, the invention provides kits comprising one or more of the chamber-forming covers of the present invention.

For example, in one series of kit embodiments, the kit comprises one or more covers of the present invention packaged with one or more electrophoresis cassettes, the covers being adapted to be applied to such cassettes.

In some embodiments, the cassettes are suitable for first dimension isoelectric focusing of IPG strips. In certain of these embodiments, the cassettes are those described in U.S. patent application publication No. 2003/0015426 and international patent publication no. WO 02/092200, the disclosures of which are incorporated herein by reference in their entireties; in certain of these embodiments, the cassettes are IPGRunner cassettes (Invitrogen Corp., Carlsbad, Calif. USA).

In some embodiments of such kits, an equal number of covers and cassettes are provided.

The kits of the present invention can comprise chamber-forming covers of the present invention and one or more fluid solutions to be used within a chamber formed by such cover, such as a solution adapted to reducing proteins focused within IPG strips, or a solution adapted to alkylating proteins focused within an IPG strip, a visible stain, or an agent capable of fluorescing, such as a biarsenical fluorophore, or a natural or artificial enzyme substrate, which may, for example, be used to detect, visualize, and/or quantify the presence of one or more enzymes present within the separation medium.

In some embodiments, the kit comprises one or more covers, one or more cassettes, and one or more fluid solutions.

In some embodiments of the kits of the present invention, the kits further comprise one or more precast gels, with or without solid supports, either fully hydrated or rehydratable. In certain of these embodiments, the kits comprise one or more IPG strips. In some of these embodiments, the kit further comprises one or more cassettes, the cassettes adapted to accept the gels or strips included within the kit. In yet other embodiments, the cassettes are provided with gel or gel strip already resident therein or thereupon.

The cover, methods, and kits of the present invention provide significant advantages, particularly (but not exclusively) in the equilibration of IPG strips prior to second dimension separation.

In particular, when the IPG strips have been focused within the channels of a cassette, such as the Invitrogen IPGRunner™ cassette, the cover and methods of the present invention permit equilibration of the strips without additional, individual, handling. The strips remain horizontal, in "native" position, and yet are adequately exposed to equilibration buffer. And the strips do not float free. As a result, they are less prone to damage and consequent loss of analytical resolution.

In addition, particularly in high throughput applications involving a plurality of gels, such as IPG strips, the chamber-forming cover significantly reduces the number of manual operations, resulting in significant time savings.

EXAMPLE 1

Exemplary Use

Exemplary instructions are provided below to equilibrate ZOOM® Strips (Invitrogen Corp., Carlsbad, Calif.) for second dimension separation after completion of IEF in an IPGRunner™ Cassette (Invitrogen Corp., Carlsbad, Calif.) using an exemplary embodiment of a chamber-forming electrophoresis cassette cover of the present invention. These exemplary instructions include an optional alkylation step using iodoacetamide to obtain the best results.

Materials needed include: (i) ZOOM® Strips in a ZOOM® IPGRunner™ Cassette after IEF (both from Invitrogen Corp., Carlsbad, Calif.); (ii) 4× NuPAGE® LDS Sample Buffer (Invitrogen Corp., Carlsbad, Calif.); (iii) NuPAGE® Sample Reducing Agent (10×) (Invitrogen Corp., Carlsbad, Calif.); (iv) iodoacetamide; (v) rotary shaker (optional); (vi) NuPAGE® Novex 4–12% Bis-Tris ZOOM® Gel or Novex® 4–20% Tris-Glycine ZOOM® Gel (both from Invitrogen Corp., Carlsbad, Calif.); and (vii) a chamber-forming electrophoresis cassette cover of the present invention, substantially according to FIGS. 9 and 11 (hereinafter also denominated, "equilibration tray").

Exemplary dimensions and specifications for the equilibration tray in this embodiment are: (i) size: 12 cm×9 cm; (ii) thickness: 0.5 mm; (iii) fluid retention volume in use: 5–15 ml; (iv) equilibration tray material: thermoformed PETG (polyethylene). In this exemplary embodiment, the adhesive layer is 3M 9495MP double sided pressure sensitive adhesive (3M, Minneapolis, Minn.) with 2.8/2.3 mils of 200 MP-series adhesive on sides A and B respectively. In this embodiment, the adhesive layer is covered initially by an easy-peel release liner with a kiss-cut pull-tab, hereinafter termed an "adhesive liner", that prevents adhesion of the equilibration tray until its removal therefrom. In this embodiment, the liner and equilibration tray itself are both disposable.

In this embodiment, equilibration trays are packaged in a kit having 10 equilibration trays, and optionally further include instructions on use.

Prepare 5–15 ml buffer per equilibration tray.

To prepare buffer for equilibration: (1) dilute 4× NuPAGE® LDS Sample Buffer to 1× with deionized water; and (2) add 1.0 ml NuPAGE® Sample Reducing Agent (10×) to 9.0 ml 1× NuPAGE® LDS Sample Buffer from Step 1 in a 15 ml conical tube.

To prepare buffer for alkylation, prepare 125 mM Alkylating Solution by dissolving 232 mg of fresh iodoacetamide in 10 ml of 1× NuPAGE® LDS Sample Buffer (prepared as above) in a 15 ml conical tube.

After IEF, remove ZOOM® IPGRunner™ Cassette from the ZOOM® IPGRunner™ Mini-Cell. Blot any excess liquid from the cassette using a paper towel and ensure your hands are dry. Firmly hold the ZOOM® IPGRunner™ Cassette and peel off the film cover from the cassette with your dry hands. Avoid introducing any liquid on the cassette surface.

(Note that you may equilibrate fewer than 6 strips using the tray. In such case, remove the desired strips from the cassette and store in a sealed container at −80° C. When you are ready to equilibrate, place the strips in a cassette and proceed to equilibration as described below).

Remove one equilibration tray from its package and pull on the adhesive liner tab to remove the liner.

Hold the equilibration tray (adhesive side down) and align the tray between the two ribs (protrusions) of the cassette such that the Invitrogen logo is towards the flat end of the cassette (FIG. 17A). Place the tray on the cassette and apply firm pressure to the tray on the adhesive area with the blunt end of a pen to ensure a tight seal between the tray and cassette (FIG. 17B). A tight seal is formed when the adhesive changes from a cloudy to clear appearance.

It is important (but not absolutely necessary) to create a tight seal between the equilibration tray and ZOOM® IPGRunner™ Cassette to prevent leaks. To obtain a tight seal, press the tray firmly on the cassette using a blunt end of a pen. A tight seal is formed when the adhesive changes from a cloudy to clear appearance. To ensure a tight seal, avoid introducing any liquid in the cassette area where the ZOOM® Equilibration Tray will be placed. If necessary, remove any remaining large pieces of adhesive remaining after removal of the film cover from the cassette and before applying the equilibration tray.

Curing of the adhesive is not required.

Add 5–15 ml 1× NuPAGE® LDS Sample Buffer prepared as above with reducing agent through either spouts of the equilibration tray.

Incubate for 15 minutes on a rotary shaker or benchtop (if you notice any leaks, see note below).

Decant the buffer into a waste container using the spouts on the equilibration tray.

Add 5–15 ml alkylating solution (prepared as above) through either spout of the equilibration tray. Incubate for 15 minutes on a rotary shaker or benchtop.

Decant buffer into a waste container using the spouts of the equilibration tray.

Shake out any residual buffer.

Remove the equilibration tray from the cassette by first pulling on the corners of the tray and then firmly removing the tray. If desired, optionally use a gel knife.

Remove the equilibrated ZOOM® Strips from the ZOOM® IPGRunner™ Cassette and immediately proceed to second dimension SDS-PAGE.

Occasionally, some buffer may leak into the adhesive area (indicated by blue color in the adhesive area). Leaks are generally caused due to the reasons described below. When leaks occur, it is best to remove the tray and discard it. Dry the cassette with a paper towel and place a fresh new tray on the dried surface of the cassette.

Among the reasons for leakage is improper seal. Improper seal is caused when the tray is not firmly pressed onto the cassette or the surface of the cassette was wet when the tray was applied, preventing a tight seal. To obtain a tight seal, press the tray firmly on the cassette using a blunt plastic object. A tight seal is formed when the adhesive changes from a cloudy to clear appearance.

Another reason for leakage is excess solution. In the exemplary embodiment of the equilibration tray in this example, the tray is designed to hold ~15 ml buffer. Adding excess buffer will generate spills.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined with reference to the appended claims along with their full scope of equivalents.

What is claimed is:

1. An assemnly for contacting at least one gel with a fluid, comprising:
   a electrophoresis cassette comprising a plurality of channels open to a first face of the cassette; and
   a cover comprising:
   a cassette-contacting member,
   a least one chamber-defining member, and
   sealing means;
   wherein said cassette-contacting member comprises a first face and a second face,
   wherein said first face of said cassette-contacting member is in surface continuity with a first face of each said chamber-defining member, the continuous surface defining a first face of said cover, said first face of said cover being a cassette-proximal face of said cover;
   wherein said first face of said cassette-contacting; member is in sealing engagement with the first face of the electrophoresis cassette;
   wherein said second face of said cassette-contacting member is in surface continuity with a second face of each said chamber-defining member, the continuous surface defining a second face of said cover, said second face of said cover being a cassette-distal face of said cover;
   wherein said cassette-contacting member is disposed circumferentially around each said chamber defining member at a first elevation of said cover;
   wherein said sealing means is disposed circumferentially around each said chamber-defining member on said first face of said cassette-contacting member and in contact with said first face of said electrophoresis cassette; and
   wherein each said chamber-defining member elevates said cover first face in the direction of said cover second face from said first cover elevation to at least a second cover elevation.

2. The assembly of claim 1, wherein said cover has a single chamber-defining member.

3. The assembly of claim 1, wherein said cover has a plurality of chamber-defining members.

4. The assembly of claim 3, wherein said cover has six chamber-defining members.

5. The assembly of claim 1, wherein each said chamber-defining member has at least one fluid port, said fluid port boring through both said first and second cover faces.

6. The assembly of claim 5, wherein each said chamber-defining member has a single fluid port.

7. The assembly of claim 5, wherein each said chamber-defining member has a plurality of fluid ports.

8. The assembly of claim 7, wherein each said chamber-defining member has two fluid ports.

9. The assembly of claim 1, wherein said cassette-contacting member is integral to each said chamber-defining member.

10. The assembly of claim 9, wherein said cover is molded from a single part.

11. The assembly of claim 10, wherein said single part is plastic.

12. The assembly of claim 11, wherein said plastic is a thermoformable plastic.

13. The assembly of claim 12, wherein said thermoformable plastic is selected from the group consisting of polypropylene, polyethylene, and polyvinylchlorides.

14. The assembly of claim 11, wherein said plastic is injection moldable.

15. The assembly of claim 14, wherein said plastic is selected from the group consisting of: polycarbonate, polystyrene, acrylic, ABS, polyvinylchloride, polypropylene, polyethylene and plasticized alloys of each.

16. The assembly of claim 1, wherein said sealing means includes an adhesive layer.

17. The assembly of claim 16, wherein said adhesive layer includes an acrylic adhesive.

18. The assembly of claim 16, wherein said adhesive layer includes a rubber adhesive.

19. The assembly of claim 17, wherein said acrylic adhesive is disposed on both sides of a polyethylene or polyvinylchloride tape.

20. A method of contacting a gel immobilized within or upon a cassette to a fluid volume, the method comprising:
   assembling a cover having at least one fluid retaining chamber on a first face of an electrophoresis cassette that comprises a plurality of channels, said first cassette face being in fluid communication with at least one gel residing in at least one of said channels; and then
   introducing a fluid into said chamber,
   wherein said cover comprises a cassette-contacting member, at least one chamber-defining member, and sealing means;
   wherein said cassette-contacting member comprises a first face and a second face,
   wherein said first face of said cassette-contacting member is in surface continuity with a first face or each said chamber-defining member, the continuous surface defining a first face of said cover, said first face of said cover being a cassette-proximal face of said cover;
   wherein said first face of said cassette-contacting member is configured to contact the first face of the electrophoresis cassette at a first elevation of said cover;
   wherein a second face of said cassette-contacting member is in surface continuity with a second face of each said chamber-defining member, the continuous surface defining a second face of said cover, said second face of said cover being a cassette-distal face of said cover;
   wherein said cassette-contacting member is disposed circumferentially around each said chamber-defining member at said first elevation of said cover;
   wherein said sealing means is disposed circumferentially around each said chamber-defining member on said cassette-contacting member first face; and
   wherein each said chamber-defining member elevates said cover first face in the direction of said cover second face from said first cover elevation to at least a second cover elevation.

21. The method of claim 20, further comprises the antecedent step of bringing said gel into fluid communication with a first face of said cassette.

22. The method of claim 20, wherein said gel is part of an immobilized pH gradient strip.

23. A disposable cover for assembling at least one fluid retaining chamber on a first face of an electrophoresis cassettes comprising:
   a cassette-contacting member; and
   at least one chamber-defining member;
   wherein said cassette-contacting member comprises a firs face and a second face,
   wherein said first face of said cassette-contacting member is in surface continuity with a first face of each said chamber-defining member, the continuous surface defining a first face of said cover, said first face of said cover being a cassette-proximal face at said cover;

wherein said second face of said cassette-contacting member is in surface continuity with a second fade of each said chambers defining member, the continuous surface defining a second face of said cover, said second face of said cover being a cassette-distal face of said cover;

wherein said first face of said cassette-contacting member is configured to contact the first face of the electrophoresis cassette;

wherein said cassette-contacting member is disposed circumferentially around each said chamber-defining member at a first elevation of said cover;

wherein an adhesive layer is disposed circumferentially around each said chamber-defining member on said first face of said cassette-contacting member, said adhesive layer covered by a removable adhesive liner; and wherein each said chamber-defining member elevates said cover first face in the direction of said cover second face from said first cover elevation to at least a second cover elevation.

24. The cover of claim 23, wherein each said chamber-defining member has at least one fluid port, said fluid port boring through both said first and second cover faces.

25. The cover of claim 23, wherein said cover is plastic.

26. A kit, the kit comprising:
at least one cover according to claim 23; and
at least one electrophoresis cassette.

27. The kit of claim 26, wherein the electrophoresis cassette comprises:
means for hydratingly lodging a prior-cast electrophoretic separation medium within an assembled enclosing member; and
means for spaced electrical communication with said enclosed medium, wherein
said spaced electrical communication means can be used to establish a voltage gradient in said enclosed separation medium sufficient to effect electrophoretic separation of analytes therein, and
said assembled enclosing member permits insertion therein of the prior-cast hydra table electrophoretic separation medium in its dehydrated state.

28. The kit of claim 26, further comprising one or more fluid solutions.

29. The kit of claim 26, further comprising at least one prior-cast separation medium.

30. The kit of claim 29, wherein said prior-cast separation medium is an IPG strip.

31. The kit of claim 27, further comprising at least one fluid solution.

* * * * *